United States Patent
Surti

(10) Patent No.: US 8,152,836 B2
(45) Date of Patent: Apr. 10, 2012

(54) VISCERAL STAPLES FOR PURSE-STRING CLOSURE OF PERFORATIONS

(75) Inventor: Vihar C. Surti, Winston-Salem, NC (US)

(73) Assignee: Cook Medical Technologies LLC, Bloomington, IA (US)

( * ) Notice: Subject to any disclaimer, the term of this patent is extended or adjusted under 35 U.S.C. 154(b) by 795 days.

(21) Appl. No.: 12/191,277

(22) Filed: Aug. 13, 2008

(65) Prior Publication Data
US 2009/0048613 A1 Feb. 19, 2009

Related U.S. Application Data

(60) Provisional application No. 60/956,580, filed on Aug. 17, 2007.

(51) Int. Cl.
*A61B 17/04* (2006.01)
(52) U.S. Cl. ............................................ 606/232
(58) Field of Classification Search ............ 606/139, 606/148, 150, 213, 215, 219, 220, 232, 75; 227/175.1–182.1
See application file for complete search history.

(56) References Cited

U.S. PATENT DOCUMENTS

| | | | |
|---|---|---|---|
| 3,339,448 A * | 9/1967 | McKee | 411/473 |
| 3,470,834 A | 10/1969 | Bone | |
| 3,814,104 A | 6/1974 | Irnich et al. | |
| 4,448,194 A | 5/1984 | DiGiovanni et al. | |
| 4,570,623 A * | 2/1986 | Ellison et al. | 606/75 |
| 4,635,637 A * | 1/1987 | Schreiber | 606/219 |
| 4,749,114 A | 6/1988 | Green | |
| 4,773,420 A | 9/1988 | Green | |
| 4,821,939 A | 4/1989 | Green | |
| 5,192,303 A | 3/1993 | Gatturna et al. | |
| 5,242,457 A * | 9/1993 | Akopov et al. | 606/144 |
| 5,318,221 A | 6/1994 | Green et al. | |
| 5,368,599 A | 11/1994 | Hirsch et al. | |
| 5,395,381 A | 3/1995 | Green et al. | |
| 5,403,329 A | 4/1995 | Hinchcliffe | |
| 5,403,342 A | 4/1995 | Tovey et al. | |
| 5,405,072 A | 4/1995 | Zlock et al. | |

(Continued)

FOREIGN PATENT DOCUMENTS
FR 2 770 764 5/1999
(Continued)

OTHER PUBLICATIONS

International Search Report; PCT/US2008/073077 (May 7, 2009).

*Primary Examiner* — Corrine M McDermott
*Assistant Examiner* — Todd J Scherbel
(74) *Attorney, Agent, or Firm* — Brinks Hofer Gilson & Lione

(57) ABSTRACT

Medical devices and related methods for closing a perforation in a bodily wall The medical device generally includes a suture having opposing first and second ends and a set of visceral staples. Each visceral staple includes a base and two tines connected to the base, the tines spaced apart two define a slot therebetween. The slot slidably receives the suture therein. Each visceral staple is attached to the bodily wall adjacent the periphery of the perforation. The ends of the suture are tensioned to reduce the distance between the visceral staples and compress the bodily wall around the perforation. The ends of the suture are secured to maintain the compression of the bodily wall and close the perforation.

23 Claims, 6 Drawing Sheets

U.S. PATENT DOCUMENTS

| | | | |
|---|---|---|---|
| 5,411,522 A | 5/1995 | Trott | |
| 5,484,451 A * | 1/1996 | Akopov et al. | 606/139 |
| 5,522,844 A * | 6/1996 | Johnson | 606/232 |
| 5,549,631 A * | 8/1996 | Bonutti | 606/232 |
| 5,573,543 A * | 11/1996 | Akopov et al. | 606/144 |
| 5,984,949 A | 11/1999 | Levin | |
| 6,152,935 A | 11/2000 | Kammerer et al. | |
| 6,228,055 B1 | 5/2001 | Foerster et al. | |
| 6,387,113 B1 * | 5/2002 | Hawkins et al. | 606/219 |
| 7,060,084 B1 | 6/2006 | Loshakove et al. | |
| RE39,841 E | 9/2007 | Bilotti | |
| RE40,237 E | 4/2008 | Bilotti et al. | |
| 7,357,287 B2 | 4/2008 | Shelton, IV et al. | |
| 7,364,061 B2 | 4/2008 | Swayze et al. | |
| 7,367,485 B2 | 5/2008 | Shelton, IV et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,404,509 B2 | 7/2008 | Ortiz et al. | |
| 7,407,074 B2 | 8/2008 | Ortiz et al. | |
| 7,407,077 B2 | 8/2008 | Ortiz et al. | |
| 7,410,086 B2 | 8/2008 | Ortiz et al. | |
| 7,416,101 B2 | 8/2008 | Shelton, IV et al. | |
| D576,278 S | 9/2008 | Nalagatla et al. | |
| 7,419,080 B2 | 9/2008 | Smith et al. | |
| 7,422,139 B2 | 9/2008 | Shelton, IV et al. | |
| 7,451,904 B2 | 11/2008 | Shelton, IV | |
| 7,455,208 B2 | 11/2008 | Wales et al. | |
| 7,461,574 B2 * | 12/2008 | Lewis et al. | 81/57.37 |
| 7,485,124 B2 | 2/2009 | Kuhns et al. | |
| 2002/0161401 A1 * | 10/2002 | Steiner | 606/232 |
| 2004/0138705 A1 * | 7/2004 | Heino et al. | 606/219 |
| 2004/0220596 A1 | 11/2004 | Frazier et al. | |
| 2006/0015144 A1 * | 1/2006 | Burbank et al. | 606/219 |
| 2006/0155288 A1 | 7/2006 | Little et al. | |
| 2006/0241691 A1 | 10/2006 | Wilk | |
| 2008/0048002 A1 | 2/2008 | Smith et al. | |
| 2008/0114378 A1 | 5/2008 | Matsushita | |
| 2008/0140095 A1 | 6/2008 | Smith et al. | |
| 2008/0147116 A1 | 6/2008 | Smith et al. | |
| 2008/0172088 A1 | 7/2008 | Smith et al. | |
| 2008/0208161 A1 | 8/2008 | Kaji et al. | |
| 2008/0208214 A1 | 8/2008 | Sato et al. | |
| 2008/0208251 A1 | 8/2008 | Weadock et al. | |
| 2008/0228199 A1 | 9/2008 | Cropper et al. | |
| 2008/0228202 A1 | 9/2008 | Cropper et al. | |
| 2008/0269566 A1 | 10/2008 | Measamer | |
| 2008/0281354 A1 | 11/2008 | Cropper et al. | |
| 2008/0296344 A1 | 12/2008 | Cropper et al. | |
| 2008/0300608 A1 | 12/2008 | Measamer | |
| 2008/0300624 A1 | 12/2008 | Schwemberger et al. | |
| 2008/0300627 A1 | 12/2008 | Measamer et al. | |
| 2009/0069822 A1 | 3/2009 | Takahashi et al. | |
| 2009/0204130 A1 | 8/2009 | Kantsevoy et al. | |
| 2010/0160931 A1 * | 6/2010 | Karpiel et al. | 606/139 |

FOREIGN PATENT DOCUMENTS

| | | |
|---|---|---|
| WO | WO 2005/086885 | 9/2005 |

\* cited by examiner

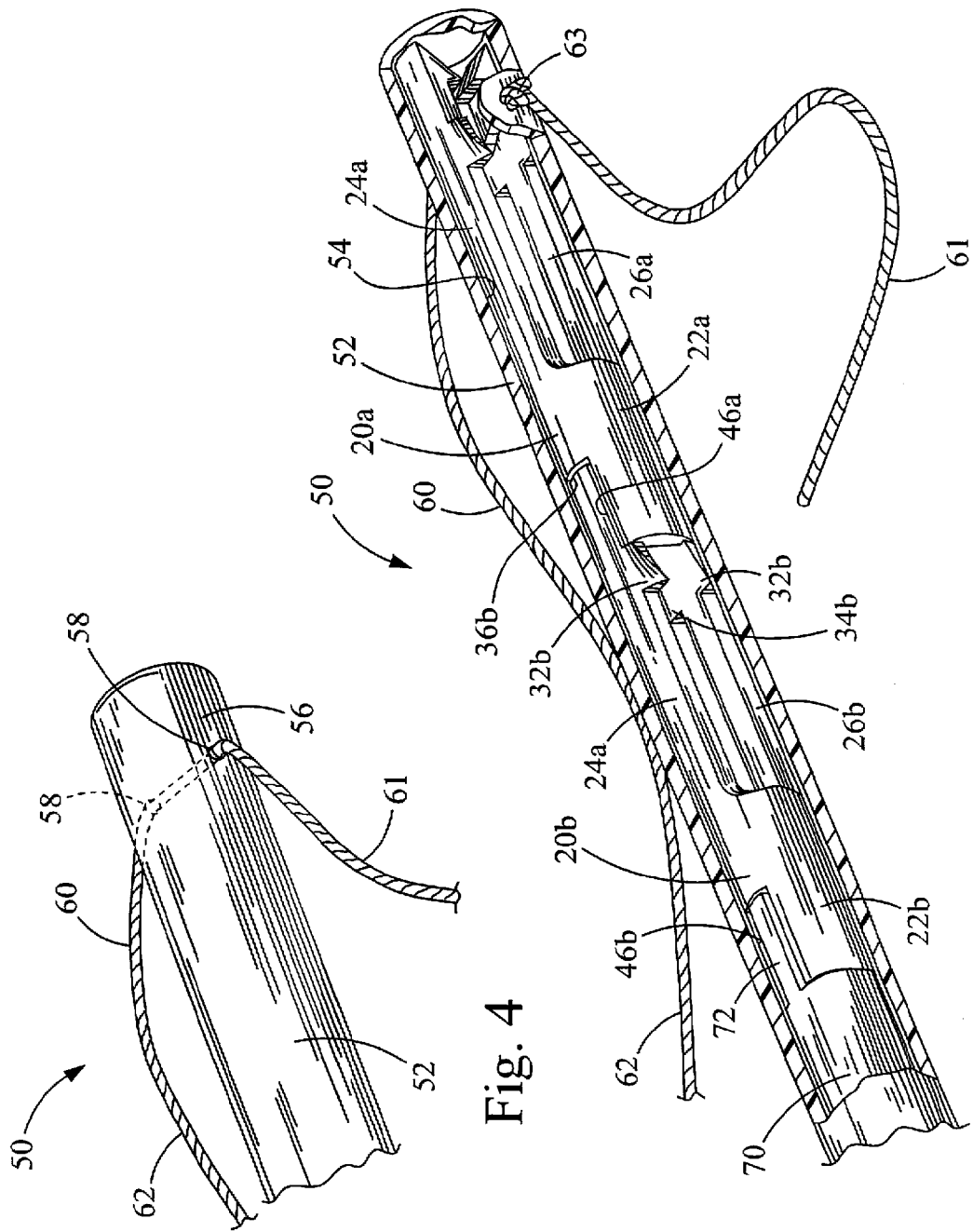

VISCERAL STAPLES FOR PURSE-STRING CLOSURE OF PERFORATIONS

CROSS-REFERENCE TO RELATED APPLICATIONS

This application claims the benefit of U.S. Provisional Application Ser. No. 60/956,580, filed on Aug. 17, 2007, entitled "VISCERAL STAPLES FOR PURSE-STRING CLOSURE OF PERFORATIONS" the entire contents of which are incorporated herein by reference.

FIELD OF THE INVENTION

The present invention relates generally to visceral stapes for closing perforations in tissue.

BACKGROUND OF THE INVENTION

Perforations in the walls of internal organs and vessels may be naturally occurring, or formed intentionally or unintentionally. In order to permanently close these perforations and allow the tissue to properly heal, numerous medical devices and methods have been developed employing sutures, adhesives, clips, and the like. One class of such devices is commonly referred to as suture staples or visceral staples. In certain applications, the staples themselves hold the edges of a perforation together, and in others they are used with sutures to draw the perforation closed. Visceral staples of the latter type have been successfully used in closing perforations, but are not without their drawbacks.

For example, when a series of staples are placed around a perforation, all of the individual sutures connected to the staples must be collected and connected together. It can often be difficult to properly tension each of the individual sutures to ensure proper approximation of the tissue around the perforation and complete closure thereof. This is especially critical within the gastrointestinal tract, where the travel of bacteria-laden fluids outside of the tract may cause unwanted and sometimes deadly infection.

BRIEF SUMMARY OF THE INVENTION

The present invention provides medical devices and related methods for closing a perforation in a bodily wall in a manner that is simple and reliable, while at the same time gives increased versatility and control over perforation closure. One embodiment of a medical device, constructed in accordance with the teachings of the present invention, generally comprises a suture having opposing first and second ends and a set of two or more visceral staples. Each visceral staple includes a base and two tines connected to the base. The tines are spaced apart to define a slot therebetween. The suture is slidably received within the slot and between the base and the bodily wall. The first and second ends of the suture are capable of being independently tensioned for translating the suture relative to each of the visceral samples enclosing the perforation. According to more detailed aspects of this embodiment tensioning of the suture reduces the distance between the visceral samples to close the perforation in a purse-string fashion. The tensioning of the suture causes compression of the bodily wall around the perforation. Each visceral staple includes barbs on the two tines, the barbs being spaced a distance away from the base such that the base is positioned near the bodily wall, thereby containing the suture immediately adjacent the bodily wall.

Another embodiment of a medical device, constructed in accordance with the teachings of the present invention, generally comprises a suture, a set of visceral staples, and a delivery catheter. Each visceral staple includes a base and two tines connected to the base, the tines being spaced apart to define a slot therebetween. The delivery catheter defines a lumen sized to receive the visceral staples. A distal end of the delivery catheter defines a pair of circumferentially spaced apertures in communication with the lumen. The suture passes through the pair of apertures and the lumen. The visceral staples are arranged in the delivery catheter such that distal translation of a visceral staple through the distal end of the delivery catheter causes the suture to enter the slot.

According to more detailed aspects of this embodiment of the medical device, as the visceral staples are sequentially placed the suture may be spooled in several manners. In one manner, the first end of the suture is fixed relative to the catheter such that the second end of the suture is spooled toward the apertures as a set of visceral staples are distally translated relative to the catheter and connected to the bodily wall. Here, the second end of the suture is preferably tensioned during distal translation of a visceral staple through the distal end of the delivery catheter. In another manner, the first and second ends of the suture are translatable relative to the catheter such that the first and second ends of the suture are spooled towards the apertures as a set of visceral staples are distally translated relative to the catheter and connected to the bodily wall. Here, both the first and second ends of the suture may be tensioned during distal translation of a visceral staple through the distal end of a delivery catheter. Preferably, the lumen of the delivery catheter is sized to receive each of the visceral staples in series. Each base includes a second slot sized to receive the two tines of the adjacent staple, thereby providing compact containment of the visceral staples. The two tines of each staple include a barb spaced away from a distal end of the staple, the barb not fitting within the second slot when the two tines are positioned within the slot.

According to another embodiment, a staple is provided for closing a perforation in a bodily wall in accordance with the teachings of the present invention. The staple generally comprises a base and two tines connected to the base. The tines are spaced apart to define a slot therebetween. Each of the tines defines a first barb and a second barb. The first and second barbs are longitudinally spaced apart, and further the first and second barbs are circumferentially spaced apart. According to more detailed aspects, the first barb extends radially inwardly, and the second barb extends laterally. The staple may further comprise a third barb longitudinally spaced from the first barb. The third barb also preferably extends laterally and is longitudinally aligned with the second barb. The base, the two tines and the bodily wall define a passageway receiving a suture, and the width of the passageway is preferably about equal to the diameter of the suture. This staple is preferably radiused where the two tines meet the base to provide a smooth surface for translating the suture relative to the staple.

Yet another embodiment, in accordance with the teachings of the present invention, provides a method for closing a perforation in a bodily wall using a set of visceral staples operably connected to a suture. The method generally comprises the steps of attaching each visceral staple to a proximal side of the bodily wall adjacent the periphery of the perforation. The ends of the suture are tensioned to reduce the distance between the visceral staples and compress the bodily wall around the perforation. The ends of the suture are secured to maintain the compression of the bodily wall enclosed to perforation. According to more detailed aspects, the attaching step preferably includes positioning the set of visceral staples around the perforation to permit closing of the perforation in a purse string fashion. The attaching step may include positioning the set of visceral staples sequentially around the perforation in a semi-annular or annular shape, or alternatively may comprise positioning the set of visceral anchors sequentially on opposite sides of the perforation. The tensioning step preferably includes independently tensioning the ends of the suture.

BRIEF DESCRIPTION OF THE DRAWINGS

The accompanying drawings incorporated in and forming a part of the specification illustrate several aspects of the present invention, and together with the description serve to explain the principles of the invention. In the drawings:

FIG. 4 is a perspective view of a medical device employing the visceral staples depicted in FIGS. 1-3;

FIG. 5 is a perspective view similar to FIG. 4, partially cut away to illustrate the visceral staples of FIGS. 1-3;

DETAILED DESCRIPTION OF THE INVENTION

Figure 1:
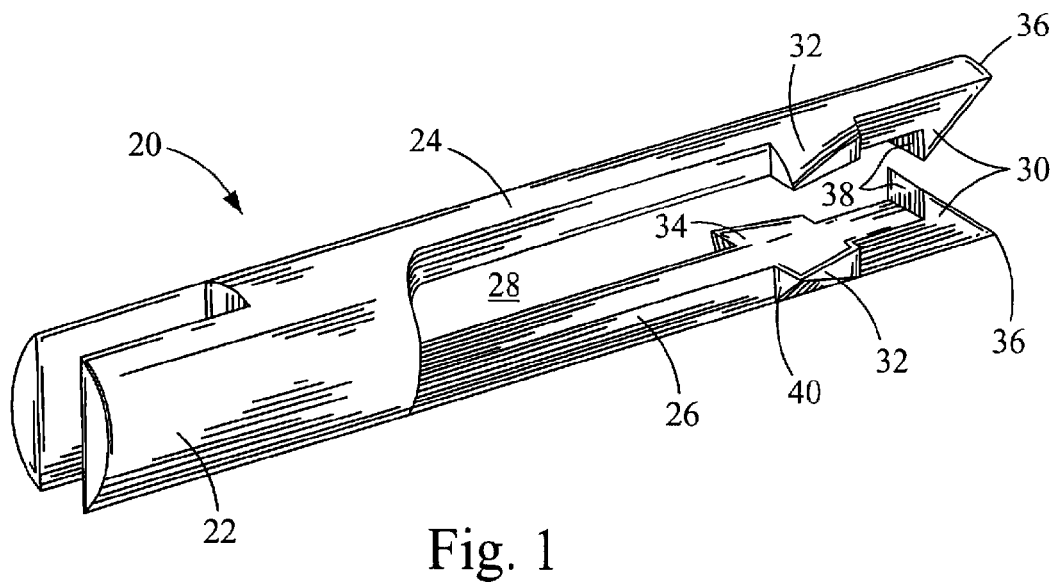
FIG. 1 is a perspective view of a visceral staple constructed in accordance with the teachings of the present invention.
Figure 2:
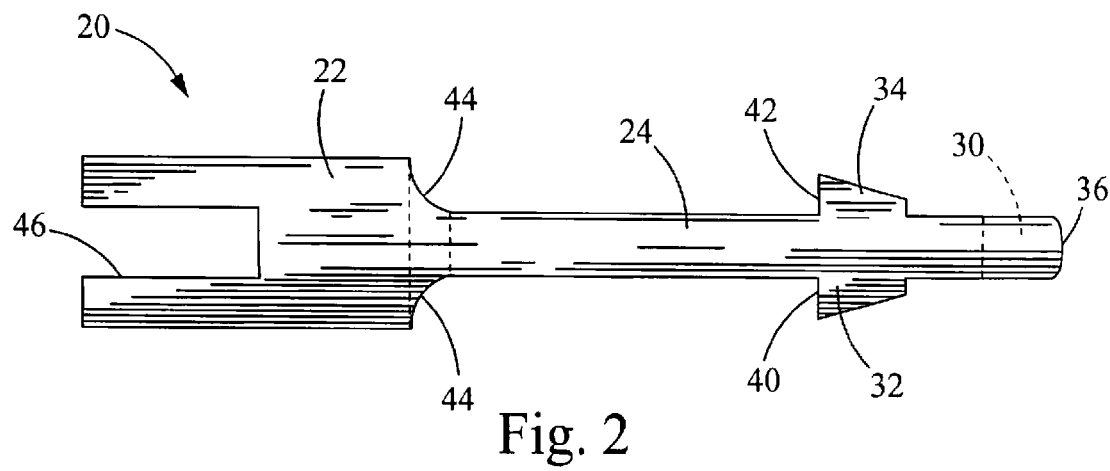
FIG. 2 is a plan view of the visceral staple depicted in FIG. 1.
Figure 3:
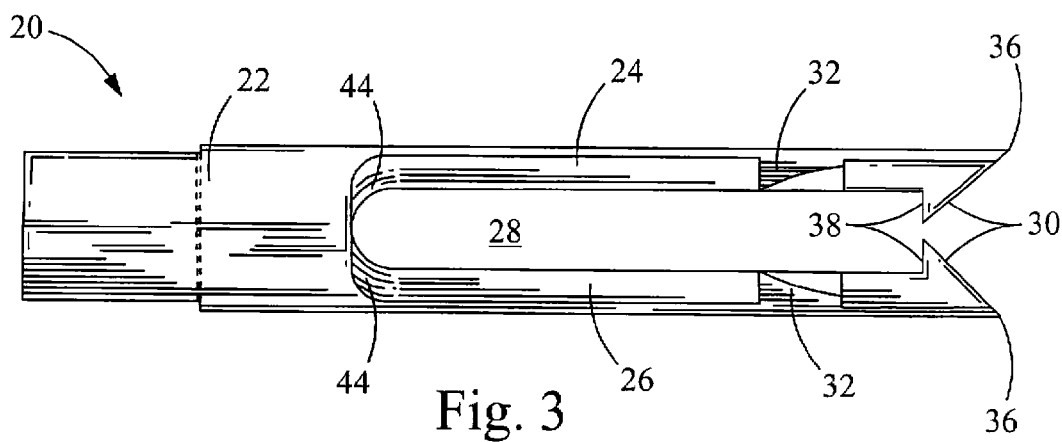
FIG. 3 is a side view of the visceral staple depicted in FIG. 1.

Turning now to the figures, FIGS. 1-3 depict a visceral staple 20 constructed in accordance with the teachings of the present invention. The staple 20 generally includes a base 22 and two tines 24, 26 connected to the base 22. The tines 24, 26 are laterally spaced apart to define a slot 28 therebetween. The visceral staple 20 is utilized to connect a suture 60 to tissue 80, as will be later described herein with reference to FIGS. 6-12. Generally, the visceral staples 20 receive the suture 60 within the slot 28, and provide for translation of the suture 60 within the slot 28. In this manner, a set of staples 20 may be utilized to form a purse-string type closure, as will also be discussed in further detail herein. Each staple 20 is preferably formed of a material such as stainless steel, titanium, nitinol or other metals/alloys, although various ceramics or plastics can be employed, such as polycarbonates (PC), polyamides including Nylon (TM), polytetrafluorethylenes (e.g. PTFE and EPTFE), polyethylene ether ketones (PEEK), polyvinylchlorides (PVC), polyimides, polyurethanes, and polyethylenes (high, medium or low density), including multi-layer or single layer constructions with or without reinforcing elements. Bioresorbable polymers, such as polylactide (PLA), polyglycolide (PGA), poly-L-lactide (PLLA), poly-DL-lactide (PDLLA) and their copolymers (e.g., PGLA, PLGA), and the like may also be used for the staples 20 such that they would degrade away after the tissue has healed.

Each of the tines 24, 26 includes a first barb 30, a second barb 32 and a third barb 34. The first barb 30 is located at the distal end of the visceral staple 20, while the second and third barbs 32, 34 are longitudinally spaced apart from the first barb 30. The tines 24, 26 and first barb 30 generally include a sharp distal edge 36 for piercing tissue. The first barb 30 also extends radially inwardly to define proximal facing shoulder 38. The shoulder 38 serves to prevent backward migration of the visceral staple 20 from the tissue. The second and third barbs 32, 34 extend laterally from the tines 24, 26. It can be seen that the second and third barbs 32, 34 are circumferentially spaced from the first barb 30. The second and third barbs 32, 34 are longitudinally aligned along the first and second tines 24, 26, and define proximally facing shoulders 40, 42, respectively, which also serve to prevent backward migration of the visceral staple 20 from tissue.

In order to accommodate the relative translation between the suture 60 and staple 20, the portions of the staple 20 where the tines 24, 26 meet the base 22 have a radiused portion 44 to provide for smooth relative translation. Preferably, the width of the slot 28 is about equal to the diameter of the suture 60, or a few times (e.g., 5 times) larger than the diameter of the suture 60. The base 22 of the visceral staple 20 also includes a second slot 46 which is sized to receive the distal ends of the tines 24, 26 of an adjacent visceral staple 20, as shown in FIG. 5. The receipt of adjacent tines 24, 26 in the second slot 46 allows for force and torque transmission through a set of multiple staples 20. Many variations of this interrelation provided by second slot 46 are envisioned; e.g. the base 22 may include a tab or other projection that is sized to fit between the tines 24, 26 of adjacent staples 20, and different socket-like arrangements can be employed between multiple staples 20 and any pusher used to advance the staples, as will be described in detail below.

It will be recognized by those skilled in the art that the tines and barbs may take many different shapes and constructions. For example, the tines may have a hollow construction, or a solid construction as shown. While two tines have been depicted, more than two tines may be readily employed in a visceral staple in accordance with the teachings of the present invention. The barbs may be formed by any resistant features, such as flat or angled surfaces, expandable surfaces or structures, or any structure that increases the force required for the tines to translate back out of the tissue.

Turning now to FIGS. 4 and 5, a medical device 50 for closing a perforation in a bodily wall will now be discussed. Generally, the medical device 50 includes a plurality of visceral staples 20, a delivery catheter 52, and a suture 60. Although two visceral staples 20a, 20b, have been depicted in FIG. 5, any number of staples 20 may be employed in conjunction with the present invention. The delivery catheter 52 defines a lumen 54 sized to receive a set (i.e. two or more) of visceral staples 20a, 20b. The visceral staples 20a, 20b are arranged in series within the lumen 54 as shown in FIG. 5. The relative position of the staples 20a, 20b is maintained by the distal ends of tines 24, 26 being received within the second slot 46 defined by the base 22 of adjacent visceral staples 20.

A distal end 56 of the delivery catheter 52 includes a pair of circumferentially spaced apertures 58. The apertures 58 are preferably spaced apart about 180 degrees, although any degree of spacing may be employed. The suture 60 is strung through the apertures 58 such that the suture 60 extends through the lumen 54 of the delivery catheter 52. Accordingly, distal translation of a visceral staple 20 through the distal end 56 of the catheter 52 causes the suture 60 to pass between the tines 24, 26 and enter the slot 28 of the visceral staple 20. A pusher 70 is slidably received within the lumen 54 of the catheter 52, and is used to distally translate the set of visceral staples 20a, 20b. It will be recognized that the pusher 70 may take many forms, including solid rods, tubular cannulas or catheters having sufficient strength to transmit force from the medical professional (outside the body) to the visceral staples 20. Preferably, the pusher 70 includes a tab 72 which is sized to be received within the second slot 46 of the most proximal visceral staple 20b. In this manner, the pusher 70 may be used to both distally translate the visceral staples 20a, 20b, and also circumferentially rotate the staples to properly orient the tines 24, 26 relative to the suture 60.

It can also be seen that the second and third barbs 32b, 34b of visceral staple 20b press against a proximal end of the base 22a of the first visceral staple 20a. The longitudinal spacing of barbs 30b and barbs 32b, 34b relative to the size of the second slot 46a prevents the sharp edge 36b of the visceral staple 20b from being blunted or otherwise deformed by being pressed against the first visceral staple 20a. At the same time, force transmission is still provided through the pusher 70 to the second visceral staple 20b and to the first visceral staple 20a. It will be recognized by those skilled in the art that the medical device 50 may simply comprise the suture 60 and a set of visceral staples 20a, 20b, etc., and that any other delivery device may be employed in accordance with the teachings of the present invention.

As subsequent visceral staples 20 are placed within tissue, additional suture material may be spooled from either the first end 61 or second end 62 of the suture, or from both ends. Additionally, one of the suture ends 61, 62 could be prevented from spooling, such as by tying a knot therein to prevent that end from passing through the holes 58 in the delivery catheter 52. For example, in FIG. 5 the first end 61 of the suture 60 includes a knot 63, whereby spooling of additional suture 60 is forced to occur from the second end 62. The spooling of suture 60 will be discussed in more detail hereinbelow.

Figure 6:
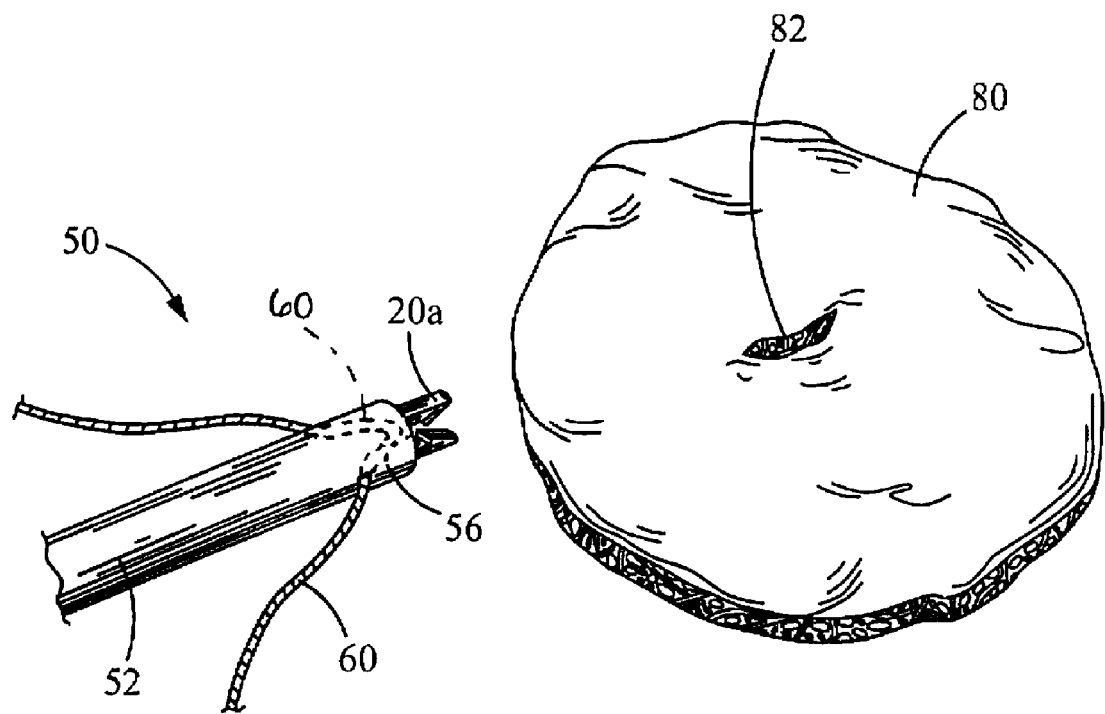
FIGS. 6-12 are plan views and cross-sectional view illustrating a method of closing a perforation utilizing the visceral staples and medical device depicted in FIGS. 1-5.

Turning now to FIGS. 6-12, a method of closing a perforation in tissue will now be described. As shown in FIG. 6, tissue 80 will generally include a perforation 82 that is desired to be closed. Accordingly, the medical device 50 will be navigated to a location within the body proximate the perforation 82. As previously discussed, the medical device 50 generally includes the catheter 52, a suture 60, and a set of visceral staples 20. Preferably, an endoscope (not shown) is utilized to access the area, and the medical device 50 may be delivered through the working channel of the endoscope. Alternatively, other visualizing devices, such as catheter based systems, other fiber optic devices, or techniques such as fluoroscopy or ultrasound may be employed in parallel with the medical device 50.

Figure 7:
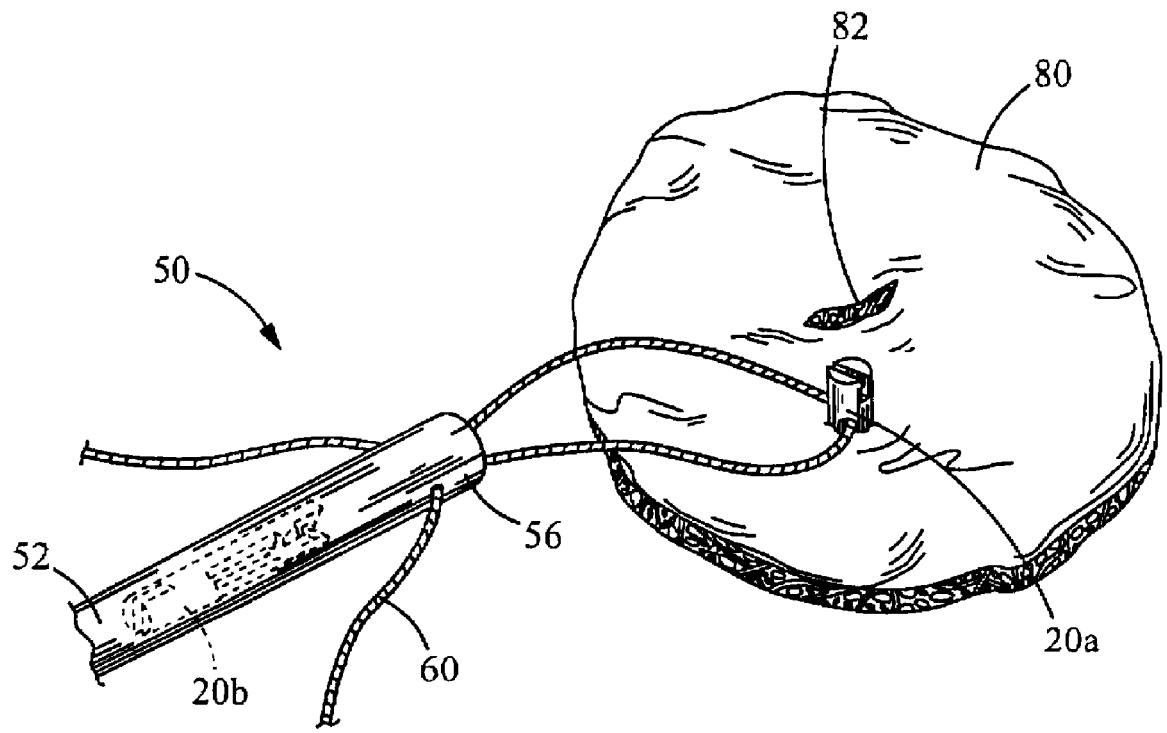

As shown in FIG. 7, the first visceral staple 20a is placed into the tissue 80 by distally translating the pusher 70 (FIG. 5) while the delivery catheter 52 is maintained in close proximity to the tissue 80. As previously discussed, the suture 60 will be maintained within the slot 28 of the visceral staple 20a, while being translatable relative thereto. That is, a passageway is formed between the base 22, tines 24, 26 and the tissue 80, the passageway slidably receiving the suture 60 when the staple 20 is placed in the tissue 80. Notably, through design of the staples' barbs 30, 32, 34, the base 22 maintains the suture 60 immediately adjacent the tissue 80 to improve perforation closure. Preferably, the first barbs 30 are spaced a distance from the base 22 about equal to or less than the thickness of the tissue 80. As such, different sized staples 20 may be designed for different applications.

Figure 8:
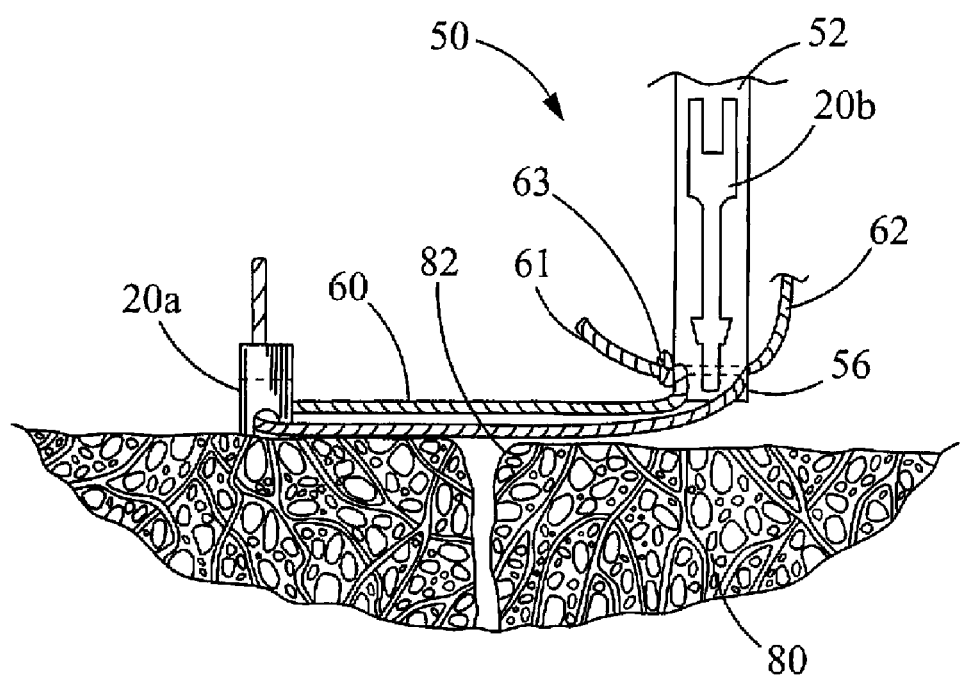

Next, the delivery catheter 52 is moved away from the first visceral staple 20a to a second location. As one example, when the first end 61 includes a knot 63, the suture 60 will be spooled from the second end 62 thereof as is shown in FIG. 8. Preferably, the second end 62 is tensioned in order to maintain a tautness of the suture 60 within the lumen 54 at the distal end of catheter 52. The tensioning may occur by hand or by a spooling device. The device 50 may be rotated as shown in FIG. 8 to position the aperture 58 that is opposite knot 63 furthest away from the placed staple 20a, to ensure to suture 60 crosses the lumen of catheter 52 for engagement by subsequent staples 20b. It will also be seen that when knot 63 is not present, the suture 60 may be spooled from either or both of the first and second ends 61, 62, in which case both ends 61, 62 are maintained in some tension to assist with the suture 60 entering the slot 28 of the distal-most staple 20 as it is translated through the distal end 56 of the delivery catheter 52.

Figure 9:
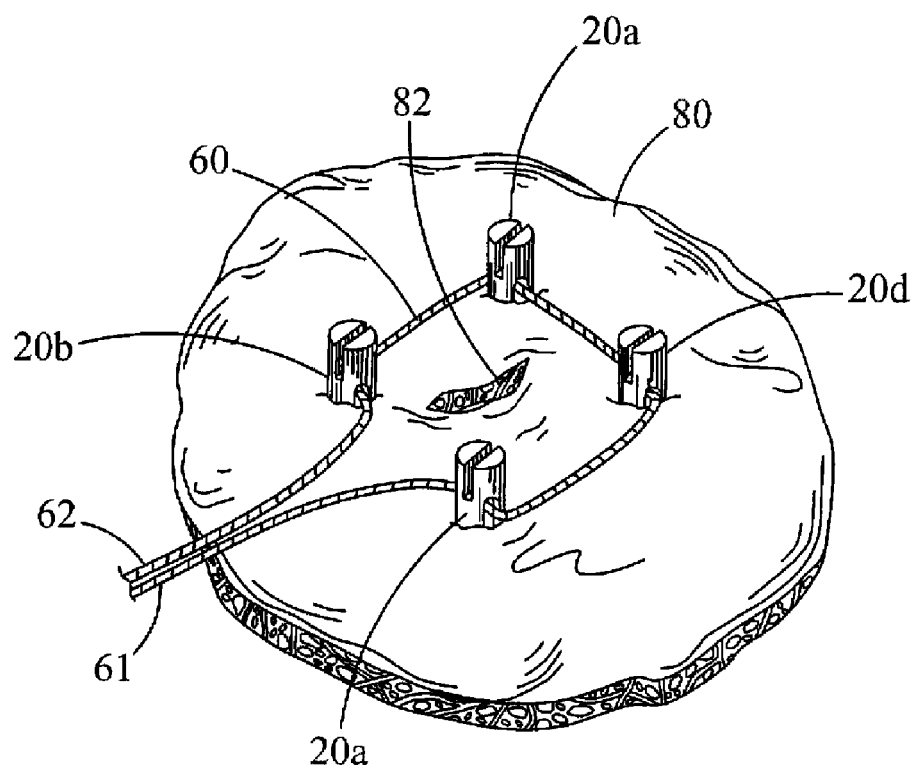
Figure 10:
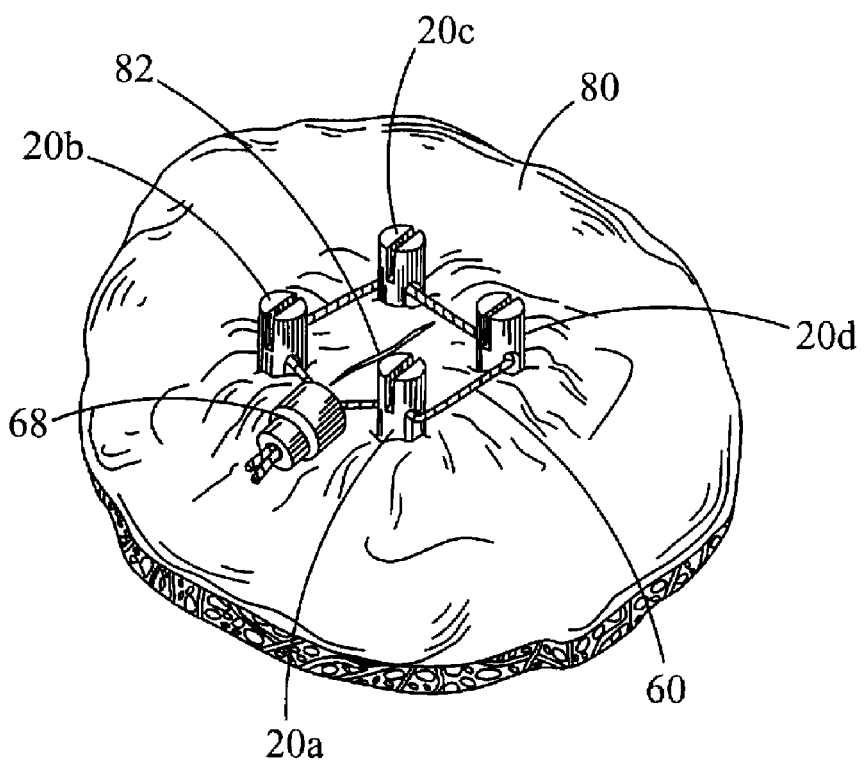
Figure 11:
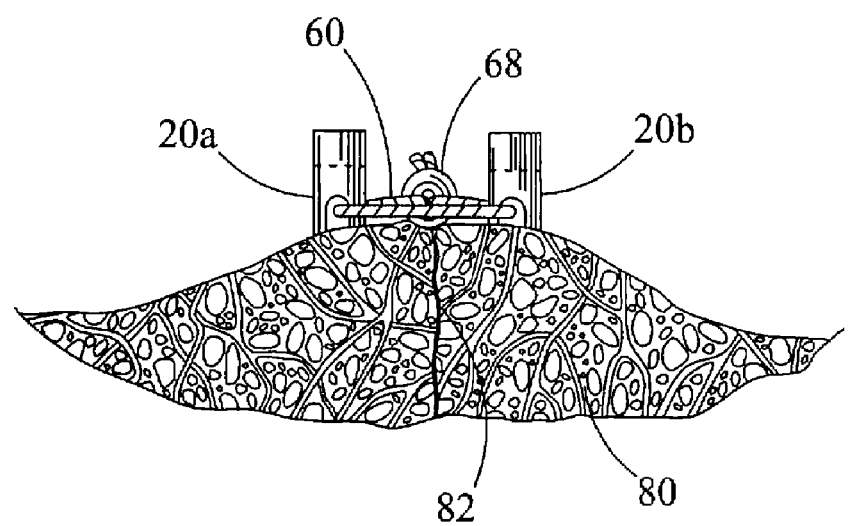
Figure 12:
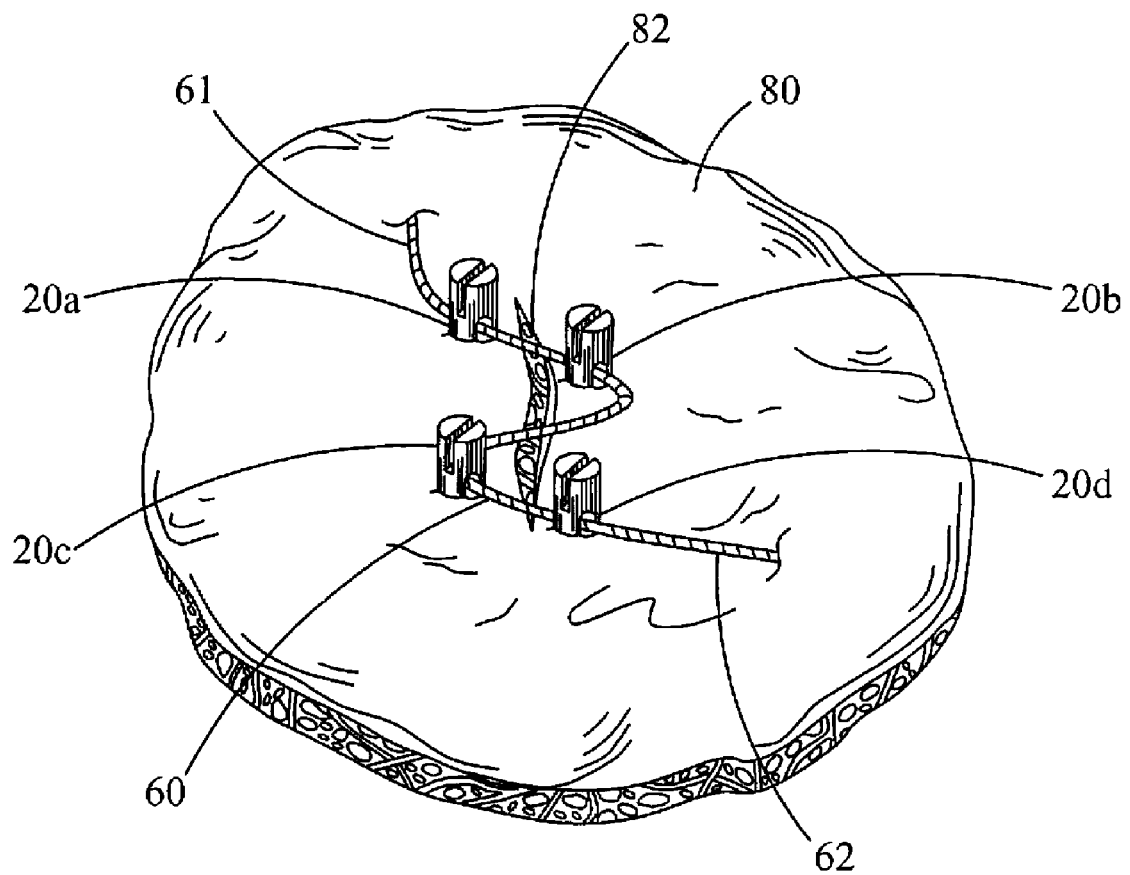

The process of placing a second visceral staple 20b is again accomplished through the distal translation of pusher 70. The above-mentioned steps are repeated to sequentially place a set of visceral staples 20a, 20b, 20c, 20d around the perforation 82 in a annular or semi-annular configuration, as shown in FIG. 9. The suture 60 and both of its ends 61, 62 are translatable relative to each of the visceral staples 20a, 20b, 20c, 20d, whereby the ends 61, 62 may be tensioned, together or independently, in order to draw the visceral staples 20, 20b, 20c, 20d towards each other and close the perforation 82 in a purse-string fashion, as shown in FIGS. 10 and 11. The ends 61, 62 of the suture 60 are fixed, such as by using a suture lock 68, or by using other devices or techniques known in the art, such as simply typing the ends 61,62 of the suture 60. As best seen in FIG. 11, the perforation 82 is therefore closed by drawing the edges of the tissue 80 around the perforation 82 into close proximity to promote healing. Although positioning of the visceral staples 20 has been shown in a semi-annular or annular shape in FIGS. 9 and 10, it will be recognized that numerous formations may be employed, such as a zig-zag formation where the visceral anchors 20 are sequentially spaced on opposite sides of a perforation 82, such as is shown in FIG. 12.

It will be recognized that the embodiments of the devices, systems and methods disclosed herein may be used with many types of tissue defects, and thus as used herein the term "perforation" includes all other tissue defects including tears, resected mucosal sites, bleeding vessels, sampled or biopsied tissue and other tissue voids which don't extend entirely through the tissue or bodily wall, as well as protrusions such as polyps, growths, hernias, aneurysms and the like.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A medical device for closing a perforation in a bodily wall, the medical device comprising:
   a suture having opposing first and second ends;
   a set of visceral staples for connecting the suture to the bodily wall, each visceral staple including a base and two tines connected to the base, the tines spaced apart to define a slot therebetween;
   a delivery catheter defining a lumen sized to receive the visceral staples, a distal end of the delivery catheter defining a pair of circumferentially spaced apertures in communication with the lumen, the suture passing through the pair of apertures and the lumen; and
   the visceral staples arranged in the delivery catheter such that distal translation of a visceral staple through the distal end of the delivery catheter causes the suture to enter the slot, wherein the first end of the suture becomes fixed in one direction relative to the catheter preventing the first end from spooling towards the apertures while only the second end of the suture is spooled towards the apertures as the set of visceral staples are distally translated relative to the catheter and connected to the bodily wall.

2. The medical device of claim 1, wherein the first end of the suture includes a knot sized larger than the apertures.

3. The medical device of claim 1, wherein the lumen is sized to receive each of the visceral staples in series.

4. The medical device of claim 1, wherein each base includes a second slot sized to receive the two tines of an adjacent staple.

5. The medical device of claim 4, wherein the two tines of each staple include a barb spaced away from a distal end of the staple, and wherein the barb abuts a proximal end of the adjacent staple when the two tines are positioned within the slot of the adjacent staple.

6. The medical device of claim 5, wherein the barb is positioned such that a sharp distal edge on the distal ends of the tines of the staple are not pressed against the adjacent visceral staple.

7. The medical device of claim 1, wherein the medical device has a deployed configuration where the visceral staples are attached to the bodily wall, and wherein the suture is slidably received above the bodily wall and between the bases and within the slots in the deployed configuration.

8. The medical device of claim 1, wherein each of the tines defines a first barb and a second barb, the first and second barbs being longitudinally spaced apart, the first and second barbs being circumferentially spaced apart.

9. The medical device of claim 8, wherein the second barb extends laterally.

10. The medical device of claim 8, further comprising a third barb longitudinally spaced from the first barb.

11. The medical device of claim 10, wherein the third barb extends laterally.

12. The medical device of claim 10, wherein the third barb is longitudinally aligned with the second barb.

13. The medical device of claim 8, wherein the second barbs are spaced from the base a distance about equal to the thickness of the bodily wall.

14. The medical device of claim 8, wherein the base and the two tines, when each visceral staple is attached to the bodily wall, define a passageway receiving the suture, and wherein the width of the passageway is between a distance about equal to the diameter of the suture and a distance about five times the diameter of the suture.

15. The medical device of claim 8, wherein the staple is radiused where the two tines meet the base to provide a smooth surface for translating the suture relative to the staple.

16. The medical device of claim 1, wherein tensioning of the suture reduces the distance between the visceral staples to close the perforation in a purse-string fashion.

17. The medical device of claim 1, wherein each visceral staple includes barbs on the two tines, the barbs spaced a distance away from the base such that the base is positioned near the bodily wall when the staple is connected to the bodily wall, thereby containing the suture immediately adjacent the bodily wall.

18. The medical device of claim 1, wherein the base of each staple is positioned near the bodily wall when the staple is affixed to the bodily wall, the suture being contained immediately adjacent the bodily wall by the two tines and base of the staple.

19. A medical device for closing a perforation in a bodily wall, the medical device comprising:
   a suture having opposing first and second ends;
   a set of two or more visceral staples for connecting the suture to the bodily wall, each visceral staple including a base and two tines connected to the base, the tines spaced apart to define a first slot therebetween, the suture being slidably received within the first slots and between the bases; and
   a delivery catheter defining a lumen sized to receive the set of visceral staples in series;
   each base including a second slot sized to receive distal portions of the two tines of an adjacent staple such that the visceral staples are rotationally connected for torque transmission;
   the first and second ends of the suture operable for independent tensioning of each of the first and second ends for translating the suture relative to each of the visceral staples and closing the perforation.

20. The medical device of claim 19, wherein the slots are shaped such that the tines and first slots of adjacent staples are circumferentially aligned to facilitate entry of the suture into the first slots as the visceral staples are longitudinally deployed through the delivery catheter.

21. The medical device of claim 19, wherein the two tines of each staple include a barb spaced away from a distal end of the staple, and wherein the barb abuts a proximal end of an adjacent staple when the two tines are positioned within the slot of the adjacent staple.

22. The medical device of claim 21, wherein the barb is positioned such that a sharp distal edge on the distal ends of the tines of the staple are not pressed against the adjacent visceral staple.

23. The medical device of claim 19, wherein the medical device has a deployed configuration where the visceral staples are attached to the bodily wall, and wherein the suture is slidably received above the bodily wall and between the bases and within the slots in the deployed configuration.

\* \* \* \* \*

UNITED STATES PATENT AND TRADEMARK OFFICE
CERTIFICATE OF CORRECTION

PATENT NO.        : 8,152,836 B2                                Page 1 of 1
APPLICATION NO.   : 12/191277
DATED             : April 10, 2012
INVENTOR(S)       : Vihar C. Surti It is certified that error appears in the above-identified patent and that said Letters Patent is hereby corrected as shown below:

In the Claims

In column 8, claim 20, line 34, after "claim 19, wherein the" insert --second--.

Signed and Sealed this
Seventeenth Day of July, 2012

David J. Kappos
*Director of the United States Patent and Trademark Office*